United States Patent [19]

Sugishima et al.

[11] Patent Number: 5,213,665
[45] Date of Patent: May 25, 1993

[54] PROCESS FOR PRODUCING 1-AMINOANTHRAQUINONES

[75] Inventors: Noboru Sugishima; Noriaki Ikeda; Yasushi Fujii, all of Himeji; Akira Inoue, Hirakata, all of Japan

[73] Assignee: Nippon Shokubai Kagaku Kogyo, Co., Ltd., Osaka, Japan

[21] Appl. No.: 717,834

[22] Filed: Apr. 8, 1991

Related U.S. Application Data

[62] Division of Ser. No. 315,591, Feb. 27, 1989.

[30] Foreign Application Priority Data

Feb. 29, 1988 [JP] Japan ................................ 63-44335
Dec. 20, 1988 [JP] Japan ................................ 63-319420
Dec. 20, 1988 [JP] Japan ................................ 63-319421

[51] Int. Cl.$^5$ .............................................. C25B 3/04
[52] U.S. Cl. .................................. 204/73 R; 204/72; 204/59 R; 552/238; 552/249; 552/251
[58] Field of Search .................. 552/238, 249, 251; 204/59 R, 72, 73 R

[56] References Cited

U.S. PATENT DOCUMENTS

| | | | |
|---|---|---|---|
| 3,875,191 | 4/1975 | Toth | 552/253 |
| 3,966,775 | 6/1976 | Fukui et al. | 552/238 |
| 3,975,411 | 8/1976 | Sameshima et al. | 552/238 |
| 3,994,932 | 11/1976 | Iwamura et al. | 552/238 |
| 4,021,456 | 5/1977 | Seha | 552/238 |
| 4,701,245 | 10/1987 | Kreh | 204/78 |
| 4,840,749 | 6/1989 | Ikeda et al. | 552/238 |
| 4,950,368 | 8/1990 | Weinberg et al. | 204/72 |
| 5,149,848 | 9/1992 | Sugishima e al. | 552/238 |

Primary Examiner—John Niebling
Assistant Examiner—Kishor Mayekar
Attorney, Agent, or Firm—Sherman and Shalloway

[57] ABSTRACT

A process for producing 1-aminoanthraquinones represented by formula (C)

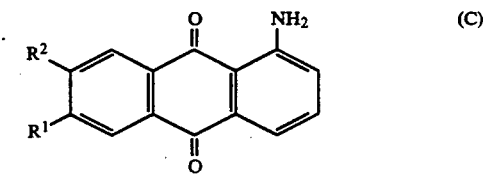

wherein $R^1$ and $R^2$, independently from each other, denote one type selected from a hydrogen atom, an alkyl group having 1 to 4 carbon atoms and a halogen atom, which comprises converting 5-nitro-1,4,4a,9a-tetrahydroanthraquinones represented by formula (A)

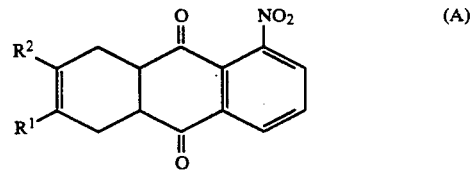

wherein $R^1$ and $R^2$ are as defined above, into 1-hydroxylaminoanthraquinones represented by formula (B)

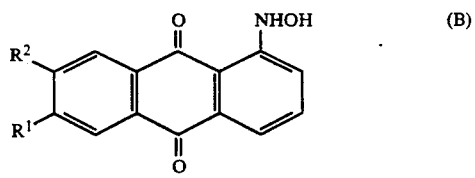

wherein $R^1$ and $R^2$ are as defined above, in the presence of a basic compound, and electrolytically reducing the resulting 1-hydroxylaminoanthraquinones in the presence of a basic compound.

9 Claims, No Drawings

PROCESS FOR PRODUCING 1-AMINOANTHRAQUINONES

This is a division of Ser. No. 315,591, filed Feb. 27, 1989.

This invention relates to a process for producing 1-aminoanthraquinones. More specifically, this invention relates to a process for producing 1-aminoanthraquinones from 5-nitro-1,4,4a,9a-tetrahydroanthraquinones via 1-hydroxylaminoanthraquinones, and a process for producing 1-aminoanthraquinones from 1-nitronaphthalene via 5-nitro-1,4-naphthoquinone, 5-nitro-1,4,4a,9a-tetrahydroanthraquinones and 1-hydroxylaminoanthraquinones.

1-Aminoanthraquinones are compounds widely used as intermediates of dyestuffs or pigments. Among them, 1-aminoanthraquinone is known as an industrially important intermediate compound.

As a process for producing 1-aminoanthraquinone using anthraquinone as a starting material, there is known a process in which anthraquinone is sulfonated and the resulting anthraquinone-1-sulfonic acid is subjected to ammonolysis to form 1-aminoanthraquinone (GB 1,370,413/1974), and a process in which anthraquinone is nitrated with concentrated nitric acid or mixed acid to form 1-nitroanthraquinone (GB 1,351,047/1974), followed by reacting it with ammonia or reducing it with an alkali sulfide or an alkali hydrosulfide. However, the sulfonation process poses problems with working environment, environmental pollution, etc. because a mercury catalyst is used in the sulfonation step. Moreover, the nitration process uses large amounts of sulfuric acid and nitric acid and is problematic in handling and treatment of a waste liquor. Besides, the resulting 1-aminoanthraquinone contains large amounts of by-products such as diamine substances and 2-amino substances. If it is used as a dyestuff intermediate, a complex purifying operation is needed. Said process cannot therefore be said to be an industrially profitable process. When a reducing agent such as an alkali sulfide, etc. is used, COD in the waste liquor becomes high, and the waste liquor treatment becomes a serious problem.

There is further known a process in which 5-nitro-1,4-naphthoquinone is subjected to the Diels-Alder reaction with 1,3-butadiene, and the resulting 5-nitro-1,4,4a,9a-tetrahydroanthraquinone is subjected to reduction by hydrogenation with a hydrogenation catalyst to prepare 1-aminoanthraquinone (GB 1,462,020/1977). This process has improved the aforesaid drawbacks and is advantageous in working environment and environmental pollution. However, said process has to use a costly catalyst such as platinum, palladium, Raney nickel, etc., and makes it hard to separate the catalyst and the product. Besides, a catalyst life is relatively short, and replacement or recovery of the catalyst is a big problem in industrializing said process.

Also known is a process for producing 1-aminoanthraquinone which comprises oxidizing 1-nitronaphthalene in a liquid phase using an acid aqueous solution containing a ceric ion, subjecting the resulting 5-nitro-1,4-naphthoquinone to the Diels-Alder reaction with 1,3-butadiene, and then reducing the obtained 5-nitro-1,4,4a,9a-tetrahydroanthraquinone with a reducing agent (EP 249,969/1987). On this occasion, the problems associated with the sulfonation process and the nitration process are conquered, and highly pure 1-aminoanthraquinone is produced industrially advantageously without causing the environmental problem. However, though said process is improved in that a theoretical amount of hydrogen needed in reduction is smaller than in case of reduing 1-nitroanthraquinone, the problem in the reduction step is still unsolved.

In the electrolysis of a mediator used in subjecting 1-nitronaphthalene to indirect electrolytic oxidation to form 5-nitro-1,4-naphthoquinone, oxidation of the mediator is conducted at an anode, but the cathodic reaction is not said to be fully utilized, and for the economical reason as well, it is desirable to effectively use the cathodic reaction. Nevertheless, it is usually difficult to balance electrolytic conditions of the anodic and cathodic reactions such as a current density, an electrical quantity, etc. For instance, when the electrolysis is carried out under optimum conditions of the anodic reaction, the conversion in the cathodic reaction does not become high enough, or conversely the reaction proceeds excessively to form by-products, lowering the selectivity. Accordingly, examples of substantially practizing the anodic/cathodic reaction are quite few. It is also thinkable that formation of hydrogen is conducted at the cathode and the resulting hydrogen is utilized in the reduction by hydrogenation in the presence of the aforesaid catalyst. In that case, the drawbacks of the reduction by hydrogenation using the catalyst still remain.

It is an object of this invention to eliminate the aforesaid drawbacks that could not be eliminated by the conventional processes and to provide a process for producing 1-aminoanthraquinones which can allow the reaction under moderate reaction conditions with good selectivity, makes easy the separation of the product and the treatment of a waste liquor and is industrially advantageous in the aspects of working environment and environmental pollution.

The present inventors have made extensive studies to develop an industrial process for producing 1-aminoanthraquinones, and consequently completed this invention.

Thus, this invention provides a process for producing 1-aminoanthraquinones represented by formula (C)

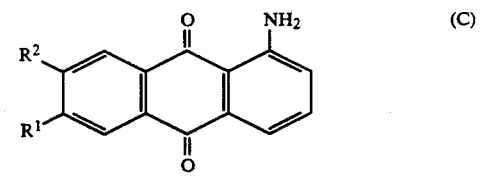

wherein $R^1$ and $R^2$, independently from each other, denote one type selected from a hydrogen atom, an alkyl group having 1 to 4 carbon atoms and a halogen atom, which comprises converting 5-nitro-1,4,4a,9a-tetrahydroanthraquinones represented by formula (A)

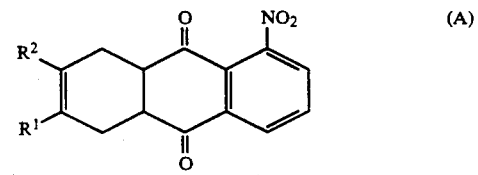

wherein R¹ and R² are as defined above, into 1-hydroxylaminoanthraquinones represented by formula (B)

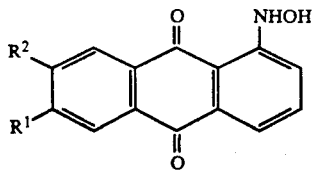

wherein R¹ and R² are as defined above, in the presence of a basic compound, and electrolytically reducing the resulting 1-hydroxylaminoanthraquinones in the presence of a basic compound.

Moreover, this invention provides a process for producing 1-aminoanthraquinones represented by formula (C)

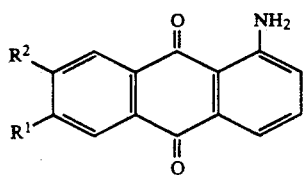

wherein R¹ and R², independently from each other, denote one type selected from a hydrogen atom, an alkyl group having 1 to 4 carbon atoms and a halogen atom, which comprises subjecting 1-nitronaphthalene to indirect electrolytic oxidation to form 5-nitro-1,4-naphthoquinone, subjecting the resulting 5-nitro-1,4-naphthoquinone to a Diels-Alder reaction with 1,3-butadienes represented by formula (E)

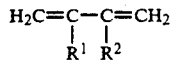

wherein R¹ and R² are as defined above, to form 5-nitro-1,4,4a,9a-tetrahydroanthraquinones represented by formula (A)

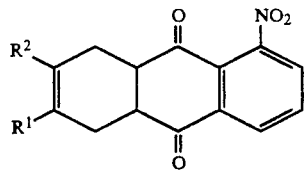

wherein R¹ and R² are as defined above, converting the resulting 5-nitro-1,4,4a,9a-tetrahydroanthraquinones into 1-hydroxylaminoanthraquinones represented by formula (B),

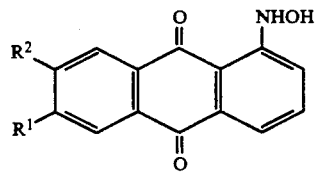

wherein R¹ and R² are as defined above, in the presence of a basic compound, and electrolytically reducing the resulting 1-hydroxylaminoanthraquinones in the presence of a basic compound, and preferably simultaneously regenerating the mediator consumed in the indirect electrolytic oxidation step and retained in the reduced state to the oxidized state.

When in the process of this invention large amounts of impurities such as dinitro substances and 6-nitro substances are contained in 5-nitro-1,4-naphthoquinone as an intermediate starting material, a purity of the product decreases as well as a toxicity of the impurities on the product becomes at issue. For this reason, 5-nitro-1,4-naphthoquinone substantially free from the impurities is desirable. Such 5-nitro-1,4-naphthoquinone can be produced by indirect electrolytic oxidation which includes contacting 1-nitronaphthalene with the mediator in an acid solution. A suitable mediator may be selected in consideration of the reaction conditions or reaction characteristics. Oxidation-reduction mediators such as Ce(IV)/Ce(III), Mn(III)/Mn(II), Mn(IV)/Mn(II) and Ag(II)/Ag(I) mediators are preferable in the aspects of selectivity, operability, safety, etc. The concentration of the mediator in an acid aqueous solution is, when Ce(IV), Mn(III), Mn(IV) or Ag(II) is used as a main oxidizing agent, preferably 0.1 to 10 mols/liter, more preferably 0.3 to 5 mols/liter, most preferably 0.5 to 3 mols/liter. Where the concentration is too high, the oxidizing agent is precipitated and slurried or the viscosity of the solution increases, for which stirring is insufficient to hinder the reaction. Meanwhile, where the concentration is too low, an oxidizing force decreases or the reactor required becomes large-sized; it is thus unwanted. These oxidizing agents are reduced to Ce(III), Mn(II) and Ag(I) by the indirect electrolytic oxidation reaction, but they can be recovered in an acid aqueous solution layer, regenerated by electrolytic oxidation and circulated again to indirect electrolytic oxidation.

As Ce(IV)/Ce(III) oxidation-reduction mediators, Ce species dissolved or suspended in an acid aqueous solution are used. Concrete examples are a solution of cerium nitrate in a nitric acid aqueous solution, a solution of cerium methanesulfonate in a methanesulfonic acid aqueous solution, a solution of cerium carbonate in a nitric acid aqueous solution, an acetic acid aqueous solution or a methanesulfonic acid aqueous solution, substances resulting from electrolytic oxidation of these solutions, etc.

As Mn(III)/Mn(II) and Mn(IV)/Mn(II) oxidation-reduction mediators, Mn species dissolved or suspended in an acid aqueous solution are used. Concrete examples are a solution of manganese sulfate in a sulfuric acid aqueous solution, a solution of manganese nitrate in a nitric acid aqueous solution, substances resulting from electrolytic oxidation of these solutions, etc.

As Ag(II)/Ag(I) oxidation-reduction mediators, Ag species dissolved or suspended in an acid aqueous solution are used. Concrete examples are a solution of silver nitrate in a nitric acid aqueous solution, a suspension obtained by adding silver (II) oxide to a nitric acid aqueous solution, substances resulting from electrolytic oxidation of these solutions or suspensions, etc.

It is advisable that the temperature of the indirect electrolytic oxidation is 0° to 80° C. Irradiation with ultrasonic waves during the oxidation reaction is also effective and desirable. It is advisable that in the reaction, an inert solvent to the mediator, e.g. a nonpolar, aprotic solvent such as nitrobenzene, chlorobenzene or dichlorobenzene is used. When Ce is employed alone or as a main mediator, an acid is preferably selected from nitric acid, acetic acid and methanesulfonic acid in consideration of an oxidizing force, a selectivity and a handleability. When Ce is used as a mediator, slurries of cerium salts are not present in the reaction or electrolytic regeneration, and handling is easy. When Mn is used alone or as a main mediator, an acid used is preferably sulfuric acid, and an acid concentration is 20 to 60% by weight, preferably 35 to 55% by weight. Mn(III) can be used in the form of a sulfuric acid solution or suspension of manganese(III) sulfate. When Ag is used as a mediator, an acid used is preferably nitric acid, and an acid concentration is 20 to 60% by weight, preferably 35 to 50% by weight. Ag(II) can be used in the form of a nitric acid solution or suspension of silver-(II) oxide, and rendered in solution state after the oxidation reaction. The electrolytic oxidation for regeneration of the mediator is usually performed at the anode using an electrolytic cell with a diaphragm. It is preferably carried out simultaneously with the electrolytic reduction of 1-hydroxylaminoanthraquinones as will be later described.

Formation of 5-nitro-1,4,4a,9a-tetrahydroanthraquinones of formula (A) by the Diels-Alder reaction of 5-nitro-1,4-naphthoquinone and 1,3-butadienes of formula (E) is carried out using a suitable solvent that dissolves the 5-nitro-1,4-naphthoquinone and the 1,3butadienes. Examples of such solvent are aromatic hydrocarbons such as benzene, toluene and xylene; halogenated hydrocarbons such as dichloroethane, carbon tetrachloride and dichlorobenzene; ethers such as ethyl ether and diphenyl ether; esters such as dioctyl phthalate; ketones such as methyl acetate; alcohols such as methanol and ethanol; and cellosolves such as methyl cellosolve. The Diels-Alder reaction of 5-nitro-1,4-naphthoquinone and 1,3-butadienes is conducted, as is the case with other aromatic quinone compounds, at a temperature of usually 0° to 250° C., preferably 30° to 150° C. The reaction pressure depends on solubility of 1,3-butadienes, etc., but is usually 120 kg/cm$^2$ or less, more commonly in the range of 0 to 20 kg/cm$^2$ As the amount of the 1,3-butadiene is more than that of 5-nitro-1,4-naphthoquinone, the reaction completes more rapidly. However, when the amount is too large, it is not economical in the aspect of an apparatus. It is preferably 1 to 20 mols, more preferably 1.1 to 10 mols per mol of 5-nitro-1,4-naphthoquinone.

In the step of converting 5-nitro-1,4,4a,9a-tetrahydroanthraquinones into 1-hydroxylaminoanthraquinones in the presence of a basic compound, 5-nitro-1,4,4a,9a-tetrahydroanthraquinones are not limited to those formed by the above method but may be those formed by the other proper methods. The reaction is carried out, for example, by adding a basic compound to 5-nitro-1,4,4a,9a-tetrahydroanthraquinones at a temperature of 0° to 200° C. preferably in a solvent. Examples of the basic compound can be usually inorganic or organic basic compounds. Especially, hydroxides, carbonates and bicarbonates of metals of Groups Ia, Ib, IIa and IIb in the periodic table are preferably used. When an aqueous solvent is used, the resulting 1-hydroxylaminoanthraquinones can be well dissolved therein under basicity and fed to the subsequent step of electrolytic reduction in the form of a solution. Accordingly, operation can easily be conducted and electrical conductivity is good, so that the electrolytic reduction is smoothly carried out. An electrolyte may be added to the solvent if required. Preferable examples of the aqueous solvent are water, alcohols such as methanol, ethanol, isopropanol and ethylene glycol, ethers, e.g. cellosolves such as methyl cellosolves. They are used either singly or in combination. Above all, it is preferable to use water alone or in combination with other aqueous solvents. When a nonaqueous solvent is used in combination with an aqueous solvent, the resulting 1-hydroxylaminoanthraquinones are extracted in the aqueous solvent layer and the unreacted starting materials in the nonaqueous solvent layer respectively, so that the aqueous solvent layer can be used as such in the subsequent electrolytic reduction step.

The electrolytic reduction of 1-hydroxylaminoanthraquinones in the presence of the basic compound is another important step that characterizes the process of this invention. Said step is carried out in an electrolytic cell with a diaphragm using a solution containing 1-hydroxylaminoanthraquinones and a basic compound as a catholyte and preferably a proton donor solution as an anolyte. The catholyte can be used by adding other electrolytes thereto or in emulsion or slurry state. In the electrolytic reduction, the concentration of 1-hydroxylaminoanthraquinone in the catholyte is not particularly limited. When it is too low, electrolytic characteristics such as a current efficiency, etc. are decreased. Meanwhile, when it is too high, a viscosity of a solution is increased. Accordingly, it is preferably 0.01 to 50 parts by weight, more preferably 0.1 to 20 parts by weight, per 100 parts by weight of the catholyte.

The basic compound present in the electrolytic reduction can be ordinarily inorganic or organic basic compounds. Concrete examples thereof are, as follows.

1) Oxides, hydroxides and weak acid salts of metals of Groups Ia, Ib, IIa and IIb in the periodic table, such as magnesium oxide, calcium oxide, sodium hydroxide, potassium hydroxide, sodium bicarbonate, sodium carbonate, sodium acetate, sodium borate, sodium sulfite, sodium hydrogenphosphate, potassium phosphate, potassium permanganate, sodium chromate, sodium sulfide, sodium methylate, sodium phenolate, tetrasodium ethylenediamine tetraacetate, sodium polysulfide and sodium hydrosulfide.

2) Ammonia, ammonium carbonate and ammonia complex salt.

3) Primary amines, secondary amines, tertiary amines, quaternary amine hydroxides and other hydrogen-containing basic compounds.

Of these, hydroxides, carbonates and bicarbonates of metals of Groups Ia, Ib, IIa and IIb in the periodic table are most preferably used. By the way, the basic compound present in the electrolytic reduction step is not necessarily the same as the basic compound present in the step of converting the 5-nitro-1,4,4a,9a-tetrahydroanthraquinones into the 1-hydroxylaminoanthraquinones, but it is advisable that they are the same. The amount of the basic compound present in the electrolytic reduction step may be more than such an amount that the system can be kept basic. However, when hydroxides, oxides or weak acid salts of metals of Groups Ia, Ib, IIa and IIb in the periodic table are used as the basic compound in amounts of at least 2 equivalents based on the 1-hydroxylaminoanthraquinones, the 1-aminoanthraquinones are dissolved in the form of salts of hydroquinone isomers after the electrolytic reduction is over, making easy the handling; it is thus desirable. However, when the amounts of the basic compound are too large, the selectivity in the electrolytic reduction decreases. Accordingly, said amount is preferably less than 1000 equivalents based on the 1-aminoanthraquinones.

The electrolytic reduction is preferably carried out in an electrolytic cell comprising an anode compartment, a cathode compartment and a diaphragm in between. With an electrolytic cell having no diaphragm, an anolyte and a catholyte are mixed. Moreover, substances resulting from reduction by the cathodic reaction move to an anode and are reoxidized, or the oxidation reaction with oxygen formed in the anode occurs at times, reducing a current efficiency, a selectivity or a yield.

In case the electrolytic oxidation for regenerating the mediator is simultaneously carried out in the anode, the diaphragm is needed. Any diaphragm will do if it serves to prevent mixing of an anolyte and a catholyte. Ceramics, resins, etc. are available. Ion exchange membranes are preferable. Anion exchange membranes or cation exchange membranes are used as the ion exchange membranes. From the aspect of durability, fluorine-type ion exchange membranes are preferable. In a multi-compartment electrolytic cell, a laminate ion exchange membrane comprising a combination of an anion exchange membrane and a cation exchange membrane or ion exchange membranes different in ion exchange capacity or type, a surface-modified ion exchange membrane, etc. are available.

In the electrolytic reduction, a known electrode is usually employed as a cathode material. However, when an aqueous solvent is used as a catholyte, it is advisable to use a material having a high hydrogen overvoltage in order to prevent decrease in current efficiency due to formation of a hydrogen gas. It is also effective to use a component having a catalytic activity in the hydrogenation reaction. Concrete examples of said component are palladium, platinum, ruthenium, rhodium, nickel, cobalt, copper, lead, iron, zirconium, cadmium, silver, tin, zinc, mercury, titanium, stainless steel and graphite. They are used either singly or in combination. They may be supported on a substrate in the form of an alloy or a compound, or by plating or sintering. On the other hand, a known electrode material is used in an anode. Examples are oxide-coated electrodes such as an iridium oxide-coated titanium and platinum-iridium oxide-coated titanium, platinum-plated titanium, graphite and glassy carbon.

The electrolytic reduction can be conducted by a constant voltage method or a constant current method. The constant current method is preferable. An electrolysis current density is usually 1 to 250 mA/cm$^2$, preferably 10 to 150 mA/cm$^2$ An electrolysis temperature is not particularly limited. However, when the temperature is low, the voltage of the electrolysis increases and the viscosity of the electrolyte also increases. For this reason, said temperature is preferably 5° C. or higher. When the temperature is too high, it invites corrosion of the material or decrease in selectivity and yield. Accordingly, it is preferably 150° C. or lower, more preferably 30° to 100° C.

Even in the electrolytic reduction using the diaphragm, oxygen tends to form in the anode to give an oxidizing atmosphere. It is therefore advisable to conduct the electrolytic reduction in a non-oxidizing atmosphere.

The anolyte is not particularly limited. When an aprotic donor solution such as an acid is however used as the anolyte, there are advantages that the crystal particle diameter of the resulting 1-aminoanthraquinones becomes large, making easy the operation of separating the 1-aminoanthraquinones via filtration, etc. and that the concentration of the basic compound in the filtrate does not increase which enables recycling of the filtrate.

Examples of the proton donor solution are carboxylic acids such as acetic acid and trifluoroacetic acid, monoalcohols such as phenol, butanol, propanol, ethanol and methanol, glycols such as ethylene glycol, sulfonic acids such as methanesulfonic acid and trifluoromethanesulfonic acid, inorganic acids such as phosphoric acid, hydrochloric acid, nitric acid and sulfuric acid, and water. They may be used singly or in combination. In particular, an acid or an acid aqueous solution is preferable, and an aqueous solution of at least one of phosphoric acid, methanesulfonic acid, hydrochloric acid, nitric acid and sulfuric acid is more preferable.

The electrolytic reduction may be conducted while circulating the electrolyte outside the electrolytic cell. Preferable however are a method wherein the electrolyte is charged in an electrolytic cell to conduct the electrolytic reduction batchwise, followed by withdrawing the electrolyte and a method wherein the electrolyte continuously flows through the electrolytic cell by one pass to conduct the electrolytic reduction. In these methods, a conversion is improved and a highly pure product having a large particle diameter is afforded. There are inconveniences that because the catholyte is expanded during the electrolytic reduction, a volume of the electrolytic cell is raised, a viscosity of the catholyte is increased by the reaction to worsen a workability and the concentration of the starting material in the catholyte has to be decreased to prevent same. However, the latter method does not suffer the problems with increase in viscosity of the catholyte and its expansion during the electrolytic reduction, and can increase the concentration of the starting material in the catholyte and also improve a productivity.

Where the electrolytic reduction is carried out under a pressure of 0.1 to 25 kg/cm$^2$G, hydrogen is, if generated at the cathode, dissolved in the catholyte and effectively acts as a reducing agent to improve a current efficiency. It is moreover effective against the expansion of the catholyte during the electrolysis, so that the concentration of the starting material in the catholyte can be increased and the electrolytic reduction be conducted advantageously.

In this invention, it is effective that the anodic/cathodic reaction is run in the electrolytic reduction step, namely, the above electrolytic reduction of the 1-hydroxylaminoanthraquinones is conducted at the cathode side and simultaneously the electrolytic oxidation for regenerating the mediator consumed in the indirect electrolytic oxidation step of 1-nitronaphthalene is conducted at the anode side. As described above, because the mediator consumed in the indirect electrolytic oxidation is recovered in the acid aqueous solution layer, said aqueous solution is used as an anolyte. In such electrolytic reduction that allows the anodic/cathodic reaction, not only a cost of an electric power needed in the electrolysis can be reduced, but also electrolytic devices such as an electrolytic cell, a power source, etc. can be effectively utilized or small-sized.

The anodic/cathodic reaction does not pose a problem of imbalance of electrolytic conditions encountered in the usual anodic/cathodic reaction. That is, in the usual anodic/cathodic reaction, it is hard to determine the electrolytic conditions (a current density, an electrical quantity, etc.) convenient in both the anodic reaction and the cathodic reaction. Accordingly, when the electrolysis is conducted under optimum conditions of the anodic reaction, there are problems that a conversion in the cathodic reaction does not become high enough or conversely the reaction advances excessively to form by-products and decrease a selectivity. In this invention, on the other hand, since a necessary stoichiometric electrical quantity in the anode is several times that in the cathode, the anodic/cathodic electrolysis is performed under the electrolytic conditions of the anode. On this occasion, a selectivity in the cathode usually becomes a problem. However, under the conditions in this invention, it is 1-aminoanthraquinones or hydroquinone isomers of 1-aminoanthraquinones that are formed by reduction of 1-hydroxylaminoanthraquinones in the cathode. As the electrical quantity increases, the amounts of the hydroquinone isomers of 1-aminoanthraquinones increases. However, these isomers are returned to 1-aminoanthraquinones by simple oxidation such as air oxidation, so that a selectivity of the cathodic reaction in the anodic/cathodic electrolysis does not pose a problem.

When in the electrolytic reduction the 1-hydroxylaminoanthraquinones are subjected to hydrogenation by reduction of two electrons to directly obtain 1-aminoanthraquinones, an electrical quantity is advantageously small, but it is hard to increase a conversion of a starting material. Meanwhile, it is also possible that 1-hydroxylaminoanthraquinones are subjected to hydrogenation by reduction of four electrons to obtain hydroquinone isomers of 1-aminoanthraquinones which are then oxidized to easily obtain 1-aminoanthraquinones. In the latter case, when a hydroquinone group forms a salt under basicity and is dissolved as in hydroquinone of 1-aminoanthraquinone, the electrolytical reduction can be carried out in solution state, making easy the operation; it is thus desirable. The electrolysis may be finished in such state that hydroquinone isomers of 1-aminoanthraquinones and 1-aminoanthraquinones are co-existent. A special oxidizing agent is not needed to obtain 1-aminoanthraquinones from hydroquinone isomers of 1-aminoanthraquinones, and it can be carried out by a simple operation such as oxidation with air or oxidation with hydrogen peroxide. It is also possible to use 1-hydroxylaminoanthraquinone as an oxidizing agent.

1-Aminoanthraquinones formed by the electrolytic reduction or oxidation of hydroquinone isomers are separated by filtration or centrifugation, and properly subjected to simple treatments such as washing, drying, etc., thereby providing high-quality products. Since the basic compound is recovered as a filtrate, it can be recycled for reuse. On this occasion, it is advisable that unnecessary organic compounds contained in the filtrate are removed to prevent extra reactions or decrease in purity of the product. This is performed, for example, by passing the filtrate through an adsorption column filled with an adsorbent such as activated carbon.

As has been stated above, the process of this invention can produce 1-aminoanthraquinones industrially advantageously in the aspects of environmental pollution and production cost and with little waste liquor compared to the conventional processes.

The following Examples illustrate this invention more specifically. However, this invention is not limited thereto. Parts in said Examples are all by weight.

EXAMPLE 1

Five parts of 5-nitro-1,4,4a,9a-tetrahydroanthraquinone was added to 20 parts of ethyl cellosolve, and 50 parts of a 5% potassium hydroxide solution was further added, followed by stirring them at 60° C. for 1 hour. The resulting solution was charged in a cathode compartment of an electrolytic cell partitioned with an anion exchange membrane, and 50 parts of a 5% potassium hydroxide aqueous solution was charged in an anode compartment. A platinum-plated titanium electrode was used as an anode and graphite as a cathode, respectively. While stirring the catholyte and the anolyte, the constant current electrolysis was conducted at 40° C. with a current density of 15 mA/cm$^2$. When an electric current was passed in an electrical quantity of 10 F/mol of 5-nitro-1,4,4a,9a-tetrahydroanthraquinone used, the electrolysis was terminated.

The voltage of the electrolysis was increased irregularly as the electrolysis advanced. When the electrolysis was over, it was about 12 volts. The catholyte was withdrawn and air was passed for 1 hour. The precipitate was then filtered. The filtrate was fine crystals and the filtration took much time. The resulting filtrate was washed with water and dried to obtain 4.2 parts of 1-aminoanthraquinone having a purity of 96%.

EXAMPLE 2

A solution obtained by adding 5.0 parts of 5-nitro-1,4,4a,9a-tetrahydroanthraquinone and 50 parts of a 20% potassium hydroxide aqueous solution to 70 parts of methyl cellosolve was used as a catholyte. A 20% potassium hydroxide aqueous solution was used as an anolyte. Using a nonionic porous membrane as a diaphragm, 5 F/mol of an electric current was passed at 90° C with a current density of 10 mA/cm$^2$. As to electrodes, platinum-plated titanium electrodes were used as an anode and a cathode. The anolyte and the catholyte were circulated via a pump. As a filter was provided at an inlet of a catholyte tank, part of the electrolysis product was obtained as a filtrate on the filter. When the electrolysis was terminated, the voltage of the electrolysis was about 4.5 volts. After the electrolysis was over, the catholyte was subjected to the same operation as in Example 1 together with the fitrate on the filter. There resulted 4.3 parts of 1-aminoanthraquinone having a purity of 97%. After the electrolysis, the concentration of potassium hydroxide in the catholyte was 24% which was higher than the initial concentration.

EXAMPLE 3

The electrolysis was conducted under the same conditions as in Example 2 except that the anolyte was bubbled with nitrogen during the electrolysis. As a result, the voltage of the electrolysis was relatively stable and about 3 volts when the electrolysis was terminated. There was obtained 4.3 parts of 1-aminoanthraquinone having a purity of 99%. After the electrolysis was over, the concentration of potassium hydroxide in the catholyte was 24% which was higher than the initial concentration.

EXAMPLE 4

An aqueous solution obtained by adding 5 parts of 5-nitro-1,4,4a,9a-tetrahydroanthraquinone to 1000 parts of a 15% sodium hydroxide aqueous solution was used as a catholyte and a 15% sodium hydroxide aqueous solution as an anolyte, respectively. The electrolysis was conducted as in Example 1 except that the current density was 100 mA/cm$^2$ and the electrolysis temperature was 90° C. There resulted 4.4 parts of 1-aminoanthraquinone having a purity of 96%. Filtration of the precipitate took much time.

EXAMPLE 5

The electrolysis was conducted as in Example 2 except that 3F/mol of an electric current was used. After the electrolysis was terminated, the filtrate on the catholyte filter was water-washed and dried to obtain 2.3 parts of 1-aminoanthraquinone having a purity of 98%. After the electrolysis was over, the concentration of potassium hydroxide in the catholyte was 22% which was higher than the initial concentration.

EXAMPLE 6

Five parts of 5-nitro-1,4,4a,9a-tetrahydroanthraquinone was added to 50 parts of methyl cellosolve, and 200 parts of a 5% potassium hydroxide solution was further added at 60° C., followed by stirring them at 60° C. for 1 hour. The resulting solution was charged in a cathode compartment of an electrolytic cell partitioned with a cation exchange membrane and 250 parts of a 5% hydrochloric acid aqueous solution in an anode compartment, respectively. A platinum-plated titanium electrode was used as an anode and a nickel plate as a cathode, respectively. While stirring the catholyte, the constant current electrolysis was conducted at 40° C. with a current density of 15 mA/cm$^2$. When an electric current was passed in an electrical quantity of 10 F/mol of 5-nitro-1,4,4a,9a-tetrahydroanthraquinone used, the electrolysis was terminated.

The catholyte was withdrawn and air was passed for 1 hour. Subsequently, the precipitate was filtered with a filter paper having a particle holdability of 8 microns. A filterability was good. The resulting precipitate was water-washed and dried to obtain 4.1 parts of 1-aminoanthraquinone having a purity of 97%. The concentration of potassium hydroxide in the filtrate was unchanged.

EXAMPLE 7

Five parts of 5-nitro-1,4,4a,9a-tetrahydroanthraquinone was added to 250 parts of the filtrate in Example 6 and dissolved. Using this solution, the electrolysis was carried out as in Example 6. After the electrolysis was terminated, the same operation was conducted. Filtration was well effected. There resulted 4.2 parts of 1-aminoanthraquinone having a purity of 96%.

EXAMPLE 8

A solution obtained by adding 5.0 parts of 5-nitro-1,4,4a,9a-tetrahydroanthraquinone to 70 parts of methyl cellosolve and further adding 100 parts of a 10% potassium hydroxide solution was used as a catholyte. A 10% sulfuric acid aqueous solution was used as an anolyte. Using a nonionic ceramic porous membrane as a diaphragm, 5F/mol of an electric current was passed at 90° C. with a current density of 30 mA/cm$^2$. A platinum-plated titanium electrode was used as an anode and a stainless steel plate as a cathode, respectively. The anolyte and the catholyte were circulated via a pump. After the electrolysis was over, the same operation as in Example 1 was conducted to obtain 4.1 parts of 1-aminoanthraquinone having a purity of 96%. A filterability was good. Reusing the obtained filtrate, the same electrolysis was conducted to obtain 4.1 parts of 1-aminoanthraquinone having a purity of 96%.

EXAMPLE 9

A solution obtained by adding 5.0 parts of 5-nitro-1,4,4a,9a-tetrahydroanthraquinone to 1000 parts of a 10% sodium hydroxide solution was used as a catholyte and a 30% trichloroacetic acid aqueous solution as an anolyte, respectively. When 20 F/mol of an electric current was passed at 30° C with a current density of 100 mA/cm$^2$ without stirring the catholyte, the electrolysis was terminated. In the same way as in Example 1, 4.4 parts of 1-aminoanthraquinone having a purity of 96% was obtained. A filterability was good. Even in the electrolysis reusing the resulting filtrate, 4.4 parts of 1-aminoanthraquinone having a purity of 95% was obtained. The concentration of sodium hydroxide in the filtrate was unchanged.

EXAMPLE 10

A solution obtained by adding 1000 parts of a 10% potassium hydroxide solution to 5.0 parts of 5-nitro-1,4,4a,9a-tetrahydroanthraquinone was used as a catholyte. A 10% sulfuric acid aqueous solution was used as an anolyte. Using a cation exchange membrane as a diaphragm, 5 F/mol of an electric current was passed at 90° C. with a current density of 30 mA/cm$^2$. A platinumplated titanium electrode was used as an anode and an expanded stainless steel plate as a cathode, respectively. After the electrolysis was over, the same operation as in Example 1 was conducted to obtain 4.1 parts of 1-aminoanthraquinone having a purity of 96%. A filterability was good. Reusing the obtained filtrate, the same electrolysis was conducted to obtain 4.4 parts of 1-aminoanthraquinone having a purity of 95%. The same operation was further repeated eight times. The finally obtained 1-aminoanthraquinone had a purity of 93%.

EXAMPLE 11

The procedure in Example 10 was repeated except that the filtrate obtained by filtering 1-aminoanthraquinone was passed through an adsorption column filled with 20 cc of activated carbon to remove an organic compound. The purity of 1-aminoanthraquinone given by repeating the procedure ten times was nearly constant and 96%.

EXAMPLE 12

Twenty five parts of 5-nitro-1,4,4a,9a-tetrahydroanthraquinone and 200 parts of a 10% sodium hydroxide solution were charged in a cathode compartment of a two-compartment stainless steel electrolytic cell with a liquid contact portion coated with a fluorine resin. A 10% sulfuric acid aqueous solution was charged in an anode compartment. A cation exchange membrane reinforced with a porous ceramic sheet was used as a diaphragm, an iridium oxide-coated titanium electrode as an anode and activated nickel as a cathode, respectively. The cathode compartment was pressured with a hydrogen gas at 5 kg/cm$^2$ and the cathode compartment with a nitrogen gas at 5 kg/cm$^2$, respectively. The constant current electrolysis was carried out at 25° C. with a current density of 30 mA/cm$^2$. When an electric current was passed in an electrical quantity of 4F/mol of 5-nitro-1,4,4a,9a-tetrahydroanthraquinone used, the electrolysis was finished.

The catholyte was withdrawn and air was passed for 1 hour. Subsequently, the precipitate was filtered via a filter paper having a particle holdability of 8 microns. A filterability was very good. The obtained precipitate was water-washed and dried to obtain 21.0 parts of 1-aminoanthraquinone having a purity of 98%.

EXAMPLE 13

Five parts of 5-nitro-1,4,4a,9a-tetrahydroanthraquinone was added to 50 parts of methyl cellosolve, and 200 parts of a 5% potassium hydroxide solution was further added, followed by stirring them at 40° C. for 1 hour. The obtained solution was charged in a cathode compartment of an electrolytic cell partitioned with a cation exchange membrane and 250 parts of a 10% sulfuric acid aqueous solution in an anode compartment, respectively. A platinum-plated titanium electrode was used as an anode and a palladium on carbon electrode as a cathode, respectively. The constant current electrolysis was conducted at 40° C. with a current density of 50 mA/cm$^2$. When an electric current was passed in an electrical quantity of 5 F/mol of 5-nitro-1,4,4a,9a-tetrahydroanthraquinone used, a fresh catholyte was continuously fed to the cathode compartment at a rate of 489 parts/hr. At the same time, the catholyte was withdrawn from the cathode compartment to make constant the amount of the catholyte in the cathode compartment. Air was passed through the withdrawn catholyte for 1 hour, and the precipitate was then filtered via a filter paper having a particle holdability of 8 microns. A filterability was very good. The obtained precipitate was water-washed and dried to obtain 1-aminoanthraquinone. From the catholyte withdrawn for 10 minutes between 60 minutes and 70 minutes from the start of the continuous feeding of the catholyte, 1.37 parts of 1-aminoanthraquinone having a purity of 99% was obtained. Problems with increase in viscosity of the catholyte and its expansion were not given during the electrolysis.

EXAMPLE 14

A nitric acid solution of ammonium ceric nitrate (a concentration of a ceric ion was 2.0 mols/liter) obtained by electrolytically oxidizing a nitric acid solution of ammonium cerous nitrate was charged into a glass container fitted with a reflux condenser and a stirrer, and maintained at 70° C. To this were added 60.55 g of 1-nitronaphthalene and 100 g of nitrobenzene, and the reaction was run for about 60 minutes with stirring. After the reaction, stirring was stopped. The reaction liquid was moved to a separatory funnel and separated into an oil layer and an aqueous layer. The aqueous layer was extracted thrice with 150 g of nitrobenzene. Said aqueous layer was electrolytically oxidized until the concentration of the ceric ion became 2.0 mols/liter again, and used to the next batch reaction.

The extracted oil layer and the separated oil layer were mixed, and the amounts of 5-nitro-1,4-naphthoquinone and the unreacted 1-nitronaphthalene in the overall organic solution were measured by high-speed liquid chromatography. There was obtained 55.17 g of 5-nitro-1,4-naphthoquinone, and the amount of the unreacted 1-nitrophthalene was 2.72 g. Accordingly, the conversion to 1-nitronaphthalene was 95.5% and the yield of 5-nitro-1,4-naphthoquinone based on reacted 1-nitronaphthalene was 81.3 mol%. The overall organic layer was concentrated at about 50° C. under reduced pressure to precipitate 5-nitro-1,4-naphthoquinone, and the precipitate separated by filtration was dried under reduced pressure for 2 hours. Subsequently, a purity was measured by high-speed liquid chromatography and found to be 99.2%.

A mixture comprising 10 g of the obtained 5-nitro-1,4-naphthoquinone, 3.3 g of 1,3-butadiene and 40 ml of ethylene glycol monomethyl ether was retained in a 100-milliliter autoclave at 50° C. for 6 hours with stirring. The reaction pressure was initially 1.2 atmospheres and 1.0 atmosphere when the reaction was over. Thereafter, 60 ml of water was added to the reaction mixture and cooled to 25° C. The precipitated crystals were filtered, washed with 30 ml of methyl alcohol and dried under reduced pressure to obtain 11.9 g of white 5-nitro-1,4,4a,9a-tetrahydroanthraquinone having a purity of 98%.

Ten grams of the thus obtained 5-nitro-1,4,4a,9a-tetrahydroquinone was added to 100 g of methyl cellosolve, and 400 g of a 5% potassium hydroxide solution was further added, followed by stirring them at 40° C. for 1 hour. The resulting solution was charged in a cathode compartment of an electrolytic cell partitioned with a cation exchange membrane and 500 g of a 10% sulfuric acid solution in an anode compartment, respectively. A platinum-plated titanium electrode was used as an anode and a nickel plate as a cathode, respectively. While stirring the catholyte, the constant current electrolysis was carried out at 40° C. with a current density of 15 mA/cm$^2$. When an electric current was passed in an electrical quantity of 10 F/mol of 5-nitro-1,4,4a,9a-tetrahydroanthraquinone used, the electrolysis was terminated.

The catholyte was withdrawn and air was passed for 1 hour. Thereafter, the precipitate was filtered via a filter paper having a particle holdability of 8 microns. A filterability was good. The resulting precipitate was water-washed and dried to obtain 8.2 g of 1-aminoanthraquinone having a purity of 97%.

EXAMPLE 15

Five hundred grams of a 45% sulfuric acid aqueous solution (suspension) containing 1 mol/kg of Mn$^{3+}$ was charged in a glass container fitted with a reflux condenser and a stirrer, and maintained at 60° C. To this was added a mixture of 40g of 1-nitronaphthalene and 60 g of nitrobenzene, and the reaction was run at 65° C for 2 hours with stirring. After the reaction, the organic phase and the inorganic phase were separated from each other. The inorganic phase was extracted with 60 g of nitrobenzene, and the resulting nitrobenzene phase was added to the aforesaid organic phase. The thus obtained organic phase was concentrated to about half and cooled. The precipitated crystals were separated by filtration. Said crystals were washed with cold methanol and then dried in vacuo to obtain 5-nitro-1,4-naphthoquinone having a purity of 95.2% in a yield of 72 mol% based on reacted 1-nitronaphthalene.

Ten grams of the thus obtained 5-nitro-1,4-naphthoquinone was reacted as in Example 14 to obtain crystals of 5-nitro-1,4,4a,9a-tetrahydroanthraquinone. Ten grams of said crystals were added to 140 g of methyl cellosolve, 200 g of a 10% potassium hydroxide solution was further added. The resulting solution was used as a catholyte. The sulfuric acid aqueous solution containing Mn$^{2+}$ which was obtained after the aforesaid oxidation reaction was used as an anolyte. A Pb electrode was used as an anode. Using a fluorine-type cation exchange membrane as a diaphragm, the electrolysis was carried out at 90° C. with a current density of 300 mA/cm² until the concentration in the anode reached 1 mol/liter. A platinum-plated titanium electrode was used as a cathode.

After the electrolysis was finished, the anolyte was reused in the next oxidation reaction. The catholyte was subjected to the same operation as in Example 1 to obtain 8.2 g of 1-aminoanthraquinone having a purity of 96%. A filterability was good. Reusing the obtained filtrate, the same electrolysis was conducted to afford 1-aminoanthraquinone having a purity of 96%.

EXAMPLE 16

Five hundred grams of a 35% nitric acid aqueous solution (suspension) containing 1 mol/kg of Ag(II) was charged in a glass container fitted with a reflux condenser and a stirrer, and maintained at 65° C. To this was added a mixture of 40 g of 1-nitronaphthalene and 60g of nitrobenzene, and the reaction was performed at 65° C. for 90 minutes with stirring. After the reaction, the organic phase and the inorganic phase were separated from each other. The inorganic phase was extracted with 60 g of nitrobenzene, and the resulting nitrobenzene phase was added to the aforesaid organic phase. The thus obtained organic phase was concentrated to about half and then cooled, and the precipitated crystals were separated by filtration. The crystals were washed with cold methanol and dried in vacuo to obtain 5-nitro-1,4-naphthoquinone having a purity of 96.0% in a yield of 75 mol% based on reacted 1-nitronaphthalene.

Ten grams of the thus obtained 5-nitro-1,4-naphthoquinone was reacted as in Example 1 to obtain crystals of 5-nitro-1,4,4a,9a-tetrahydroanthraquinone. Ten grams of the crystals were added to 140 g of methyl cellosolve, and 200 g of a 10% potassium hydroxide solution was further added. The resulting solution was used as a catholyte. The nitric acid aqueous solution containing Ag(I) which was obtained after the aforesaid oxidation reaction was used as an anolyte. Ag plates were used as an anode and a cathode. Using a fluorine-type cation exchange membrane as a diaphragm, the electrolysis was performed at 90° C. with a current density of 300 mA/cm² until the concentration in the anode reached 1 mol/liter.

After the electrolysis was terminated, the anolyte was used in the next oxidation reaction. The catholyte was subjected to the same operation as in Example 1 to obtain 8.2 g of 1-aminoanthraquinone having a purity of 96%. A filterability was good. Reusing the obtained filtrate, the same electrolysis was carried out to afford 8.2 g of 1-aminoanthraquinone having a purity of 96%.

What we claim is:

1. A process for producing 1-aminoanthraquinones represented by the formula (C)

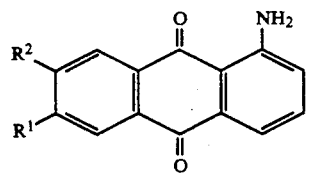

wherein $R^1$ and $R^2$, independently from each other, denote one type selected from a hydrogen atom, an alkyl group having 1 to 4 carbon atoms and a halogen atom, which consists essentially of the steps of:
subjecting 1-nitronaphthalene to indirect electrolytic oxidation by contact with a mediator to form 5-nitro-1,4-naphthoquinone;
subjecting the resulting 5-nitro-1,4-naphthoquinone to a Diels-Alder reaction with 1,3 butadienes represented by formula (E)

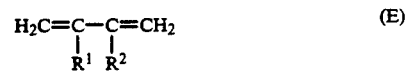

wherein $R^1$ and $R^2$ are as defined above, to form 5-nitro-1,4,4a,9a-tetrahydroanthraquinones represented by formula (A)

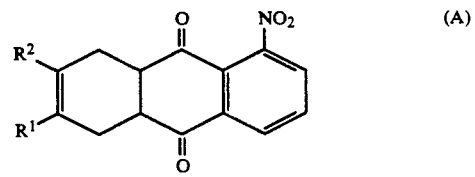

wherein $R^1$ and $R^2$ are as defined above;
converting the resulting 5-nitro-1,4,4a,9a-tetrahydroanthraquinones into 1-hydroxylaminoanthraquinones represented by the formula (B),

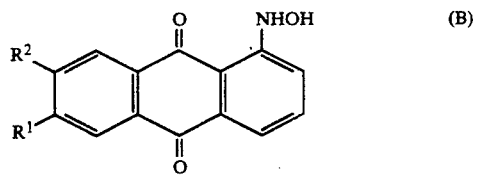

wherein $R^1$ and $R^2$ are as defined above, in the presence of a basic compound; and
electrolytically reducing the resulting 1-hydroxylaminoanthraquinones in the presence of a basic compound to produce 1-aminoanthraquinones represented by formula (C).

2. The process of claim 1 wherein at least a part of the 1-hydroxylaminoanthraquinones of formula (B) are electrolytically reduced to hydroquinone isomers of 1-aminoanthraquinones represented by formula (D)

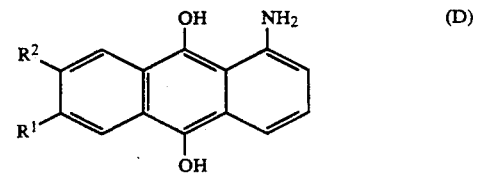

wherein $R^1$ and $R^2$, independently from each other, denote one type selected from a hydrogen atom, an alkyl group having 1 to 4 carbon atoms and a halogen atom,
during the electrolytic reduction of the 1-hydroxylaminoanthraquinones; and these hydroquinone isomers are then oxidized to produce 1-aminoanthraquinones.

3. The process of claim 1 wherein the indirect electrolytic oxidation is carried out using at least one oxidation-reduction mediator selected from Ce(IV)-

/Ce(III), Mn(III)/Mn(II), MN(IV)/Mn(II) and AG-(II)/Ag(I) mediators.

4. The process of claim 1 wherein the electrolytic reduction is carried out in an electrolytic cell comprising an anode compartment, a cathode compartment and a diaphragm in between, and the electrolytic reduction of 1-hydroxylaminoanthraquinones is conducted at the cathode, and electrolytic oxidation of the mediator is conducted at the anode to oxidize the mediator.

5. The process of claim 1 wherein the electrolytic reduction is carried out using a cathode containing at least one material selected from palladium, platinum, ruthenium, rhodium, nickel, cobalt, copper, lead, iron, zirconium, cadmium, silver, tin, zinc, mercury, titanium, stainless steel and graphite.

6. A process for producing 1-aminoanthraquinones represented by formula (C)

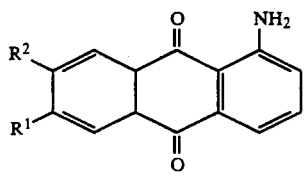

wherein $R^1$ and $R^2$, independently from each other, denote one type selected from a hydrogen atom, an alkyl group having 1 to 4 carbon atoms and a halogen atom,
which comprises:
subjecting 1-nitronaphthalene to indirect electrolytic oxidation by contact with a mediator to form 5-nitro-1,4-naphthoquinone and separating the mediator;
subjecting the resulting 5-nitro-1,4-naphthoquinone to a Diels-Alter reaction with 1,3-butadienes represented by formula (E)

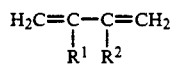

wherein $R^1$ and $R^2$ are as defined above, to form a 5-nitro-1,4,4a,9a-tetrahydroanthraquinones represented by formula (A)

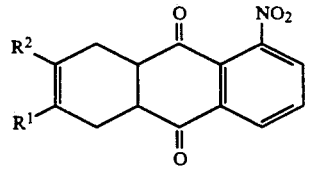

wherein $R^1$ and $R^2$ are as defined above;

converting the resulting 5-nitro-1,4,4a,9a-tetrahydroanthraquinones into 1-hydroxylaminoanthraquinones represented by formula (B).

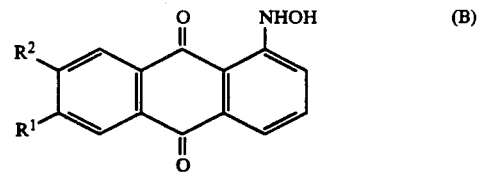

wherein $R^1$ and $R^2$ are as defined above, in the presence of a basic compound; and
electrolytically reducing the resulting 1-hydroxylaminoanthraquinones in the presence of a basic compound to produce 1-aminoanthraquinones represented by formula (C),
wherein the electrolytic reduction is carried out in an electrolytic cell comprising an anode compartment, a cathode compartment and a diaphragm in between, and the electrolytic reduction of the 1-hydroxylaminoanthraquinones is conducted at the cathode, and simultaneously the electrolytic oxidation of the separated mediator is conducted at the anode.

7. The process of claim 6 wherein at least a part of the 1-hydroxylaminoanthraquinones of formula (B) are electrolytically reduced to hydroquinone isomers of 1-aminoanthraquinones represented by formula (D)

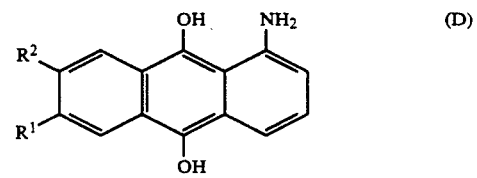

wherein $R^1$ and $R^2$, independently from each other, denote one type selected from a hydrogen atom, an alkyl group having 1 to 4 carbon atoms and a halogen atom,
during the electrolytic reduction of the 1-hydroxylaminoanthraquinones; and these hydroquinone isomers are then oxidized to produce 1-aminoanthraquinones.

8. The process of claim 6 wherein the indirect electrolytic oxidation is carried out using at least one oxidation-reduction mediator selected from Ce(IV)-/Ce(III), Mn(III)/Mn(II), Mn(IV)/Mn(II) and Ag-(II/Ag(I) mediators.

9. The process of claim 6 wherein the electrolytic reduction is carried out using a cathode containing at least one material selected from palladium, platinum, ruthenium, rhodium, nickel, cobalt, copper, lead, iron, zirconium, cadmium, silver, tin, zinc, mercury, titanium, stainless steel and graphite.

* * * * *